United States Patent [19]

Young et al.

[11] Patent Number: 4,939,088

[45] Date of Patent: Jul. 3, 1990

[54] SUSTAINED PRODUCTION OF RECOMBINANT GAMMA INTERFERON USING AN EPSTEIN-BARR VIRUS REPLICON

[75] Inventors: Janet M. Young, Washington, D.C.; Nava Sarver, Potomac, Md.; William N. Drohan, Springfield, Va.

[73] Assignee: Meloy Laboratories Inc., Springfield, Va.

[21] Appl. No.: 16,044

[22] Filed: Feb. 18, 1987

[51] Int. Cl.$^5$ ............ C12P 21/00; C12N 15/00; C12N 5/00
[52] U.S. Cl. ............ 435/69.51; 435/240.2; 435/240.26; 435/320; 424/85.5
[58] Field of Search ............ 435/68, 70, 172.3, 320, 435/235, 240.2, 240.26, 69.51

[56] References Cited

U.S. PATENT DOCUMENTS 4,686,186  8/1987  Sugden ............ 435/68

FOREIGN PATENT DOCUMENTS 2107718  5/1983  United Kingdom .

Primary Examiner—Blondel Hazel
Attorney, Agent, or Firm—Herbert H. Jervis; Martin F. Savitzky; Gilbert W. Rudman

[57] ABSTRACT

A recombinant DNA expression vector comprising an Epstein-Barr virus origin of replication, an EBNA-1 gene, a selectable marker expression cassette and a human gamma interferon expression cassette comprising a promoter region, an open reading frame encoding human gamma interferon and a polyadenylation region; a mammalian host cell transformed by said vector; and a process for producing human gamma interferon using said transformed mammalian host cell.

20 Claims, 9 Drawing Sheets

FIG.1

| MASTER CULTURE | ORIENTATION OF γ-IFN CASSETTE | U/ml/24 HRS |
|---|---|---|
| JY147-1 | —EBNA—→ γ-IFN→ HYG$^r$← — | 2750 |
| JY147-2 | —EBNA—→ γ-IFN→ —HYG$^r$← — | 2400 |
| JY147-3 | —EBNA—→ γ-IFN→ —HYG$^r$← — | 2250 |
| JY147-4 | —EBNA—→ γ-IFN→ —HYG$^r$← — | 3250 |
| JY162-1 | —EBNA—→ γ-IFN← —HYG$^r$← — | 30 |
| JY162-2 | —EBNA—→ γ-IFN← —HYG$^r$← — | 50 |
| JY162-3 | —EBNA—→ γ-IFN← —HYG$^r$← — | 65 |
| JY162-4 | —EBNA—→ γ-IFN← —HYG$^r$← — | 30 |

FIG.IA

HUMAN γ-INTERFERON EXPRESSION IN ISOLATED CELL CLONES

| VECTOR DNA | ORIENTATION OF γ-IFN CASSETTE | TOTAL NUMBER OF CLONES ANALYZED | γ-INTERFERON/U/ML/24 HOURS | | | |
|---|---|---|---|---|---|---|
| | | | ≤30 | 30-100 (56) | 200-1,000 (600) | 2,000-10,000 (5600) |
| p147 | →EBNA-1——→γ-IFN HYG$^r$→ | 11 | 0 (0%) | 0 (0%) | 8 (72.7%) | 3 (27.3%) |
| p162 | →EBNA-1——←γ-IFN HYG$^r$← | 17 | 12 (70.6%) | 3 (17.6%) | 2 (11.8%) | 0 (0%) |

|  | NS 72.4 | JY 147.62 | JY 147.64 | Kb RNA STANDARDS |
|---|---|---|---|---|

SUSTAINED PRODUCTION OF RECOMBINANT GAMMA INTERFERON USING AN EPSTEIN-BARR VIRUS REPLICON

FIELD OF THE INVENTION

This invention relates to processes for producing recombinant human immune interferon (gamma-IFN). More particularly, the invention relates to a process for production of recombinant human immune interferon in mammalian cell expression systems using an Epstein-Barr virus-derived shuttle vector.

BACKGROUND OF THE INVENTION

Interferon is a glycoprotein whose synthesis in cells is principally induced by viruses or mitogens. Interferons are classified into three major species designated alpha-IFN (leukocyte), beta-IFN (fibroblast), and gamma-IFN (immune). Interferons possess potent antiviral, anticellular, immunoregulatory, and antitumor activities. Interferon treatment of cancer and viral infections in animals has met with some success. Recent evidence suggests that infections caused by other etiological agents may yield to gamma-IFN treatment. It has been reported that gamma-IFN strongly inhibited the development of the exoerythrocytic form of *Plasmodium berghei* in the liver cells of murine hosts. Human gamma-IFN also diminished the parasitemia in chimpanzees infected with sporozoites of the human malaria parasite, *Plasmodium vivax*. In addition, initial clinical tests with human gamma-IFN in the treatment of patients with lepromatous leprosy were encouraging enough to suggest further testing for therapeutic effects of gamma-IFN in non-viral infectious diseases. Gamma-IFN, therefore, is of great interest clinically as well as academically.

In general, recombinant deoxyribonucleic acid (DNA) techniques have now become well known. An extensive technical discussion embodying most commonly used recombinant DNA methodologies can be found in *Molecular Cloning: A Laboratory Manual* (1982) by Maniatis, Fritsch and Sambrook. Genes coding for various polypeptides may be cloned by incorporating a DNA fragment coding for the polypeptide in a recombinant DNA vehicle, e.g., bacterial or viral vectors, followed by transformation of a suitable host. Previously, this host was primarily *Escherichia coli* (*E. coli*) cells. However, with the development of eukaryotic viral vectors, it is now possible to reintroduce cloned genes into their natural environment, where mechanisms involved in control of gene expression and developmental regulations can be tested. A important application of eukaryotic vectors is the production of biologically active gene products suitable for pharmacological use.

Several methods are currently in use for delivering defined foreign DNA segments into eukaryotic cells. These include physical injection of DNA, fusion of DNA containing liposomes or erythrocytes with target cells, the direct application of naked DNA onto cells in the presence of calcium phosphate and marker DNA, protoplast fusion and electroporation.

Insertion of DNA into recipient cells has also been achieved by using viral particles in which a segment of the viral genome is covalently linked to defined nucleic acid segments. One such example is the Simian Virus 40 (SV40) vector system, which offers a rapid and efficient way to introduce foreign DNAs into permissive host cells. The system is limited by the size of DNA that can be accommodated within the virus particle. Moreover, since monkey cells are permissive for SV40 replication, infection by recombinant SV40 particles culminates in cell death. SV40 DNA has not yet been exploited as a cloning vector in nonpermissive rodent cells because (i) SV40 transformation is associated with integration of the viral genome, a process that may disrupt the integrity of the foreign DNA segment of interest; and (ii) there is no indication that the gene will be active at detectable levels from the low integrated copy numbers which are sufficient for the expression of the SV40-transforming gene. Other recombinant viral particles have also been used for specific applications in gene expression. These include retroviruses for potential in vivo utility in gene therapy, vaccinia virus for human and animal vaccination, and adenovirus for in vitro gene expression.

An example of a eukaryotic expressional vector which contains viral genetic components not incorporated within a virus particle is the bovine papillomavirus (BPV) DNA. The use of this vector was originally based on the observation that the viral genome persists as an extrachromosomal plasmid in transformed cells. In this form, the cloned gene is maintained in a uniform sequence environment of the BPV minichromosome, eliminating potential problems associated with the integration of the cloned DNA into inactive regions of the host chromosome. This property was fully exploited in the establishment of BPV shuttle vector capable of replicating in prokaryotic and eukaryotic cells. Such vectors are efficient in directing the regulated expression from inducible promoters and in expressing gene products destined for intra- and extracelular location.

The BPV shuttle vector system provides an efficient method to produce high amounts of a human protein in mammalian cells. However, it is limited in its use to rodent and bovine cells, a factor which may be a disadvantage in the expression of larger human proteins. Specifically, extensive post-translational modification (i.e., glycosylation) may be species specific. Consequently, the same protein produced in a heterologous host may be immunogenic in a human subject. Additionally, certain BPV plasmids will produce a transformed phenotype when transfected into rodent cells. Therefore, studies involved with differentiated cells are not feasible due to the dedifferentiating effect of these transforming vectors.

This invention describes the application of an Epstein-Barr virus (EBV) derived vector which can overcome certain limitations of BPV expression vectors, while retaining the advantages of extrachromosomal replication an the ability to direct expression of heterologous DNAs. Defined genetic elements of the EBV genome have been shown to support stable replication of recombinant plasmids. These include the cis acting origin of plasmid replication (oriP) and the trans acting Epstein-Barr nuclear antigen (EBNA-1) protein.

We have incorporated genetic regulatory elements to direct expression of heterologous genes from the EBV-derived vectors. These include, for example, the mouse metallothionein gene I promotor or SV40 early promotor, as well as enhancer sequences, such as those derived from the long terminal repeat (LTR) region of Moloney Murine Sarcoma Virus (M-MSV) or from human cytomegalovirus. DNA sequences from SV40 which direct splicing and specify polyadenylation of transcribed RNA have also been incorporated into the EBV-derived vectors. Such modifications direct the correct expression of heterologous genes, such as human gamma interferon or human Factor VIII, in human or monkey epithelial, fibroblast or lymphoid cells transfected with EBV-derived vector DNA. In addition, these vectors contain a dominant selectable marker, the gene for hygromycin phosphotransferase, the expression of which renders mammalian cells resistant to the antibiotic hygromycin-B (hyg$^r$).

In cell lines having a large number of ribosomes, such as lymphocytes, it has been found that hygromycin-B is 3 to 10 times more toxic than G418, another aminoglycoside commonly used for selection of cells which have taken up DNA. Hygromycin-B may, therefore, be preferred to G418 in these cell types since it ensures a mor rapid selection of those cells harboring the DNA of interest. An additional advantage to using the EBV derived vectors is that the recipient host does not exhibit a transformed phenotype. Here we demonstrate the use of Epstein-Barr virus replicons as mammalian expression vectors.

BRIEF DESCRIPTION OF THE INVENTION

The present invention has made it possible to provide readily available quantities of any desirable human protein, including human immune interferon, Factor VIII, PDGF, or collagen III, and to demonstrate the efficacy of EBV vectors for expression of mammalian-derived complementary DNAs (cDNAs). This has been achieved by the application of recombinant DNA methodology for the construction of cloning vehicles encoding the desired human protein, screening of positive recombinant cells, and isolation/purification procedures for recovering human protein essentially free of other proteins of human origin.

Accordingly, the present invention provides an Epstein-Barr virus derived expression vector with the unique capability of stable expression of any desirable human protein in a host cell of the same species. B. Sugden of the University of Wisconsin modified the Epstein Barr virus so as to contain two EBV-derived genetic elements, the EBNA-1 gene and ori P, as well as the hygromycin phosphotransferase (hph) expression cassette, the pUC12 derived multiple cloning site, and the pBR322 origin of replication and beta-lactamase gene. In the present invention, the above vector is further modified to express human polypeptides by adding a human polypeptide (HP) transcriptional cassette to the construction. The HP transcriptional cassette is comprised of (1) RNA processing elements including the SV40 poly-adenylation and splice signals, (2) the mouse metallothionein gene I promoter or the SV40 promoter and (3) an enhancer such as derived from Moloney murine sarcoma virus (M-MSV) or human cytomegalovirus (HCMV). The EBV derived construction with the addition of the HP transcriptional cassette provides a means of expression for any desirable protein. Any cDNA, once isolated can be ligated into the HP transcriptional cassette and be stably expressed as directed by the regulatory elements described above.

Two features of the EBV-modified system make it desirable for production of pharmacologically important proteins. Correct post-translational modifications (glycosylation, phosphorylation, etc.) of human proteins may necessitate expression in a human cell line; a requirement not met by other stable expression vector systems. In addition, utilization of a human cell line to produce a human protein may eliminate any immunogenic reaction (response to incorrect tertiary structure of the protein) in a human subject which may result from production of the protein in a heterologous host cell line. The expression of human gamma interferon is illustrated below by the ligation of gamma-IFN cDNA into the HP transcriptional cassette (designated gamma-IFN transcriptional cassette in this invention). However, any other cDNA for a human protein, i.e., Factor VIII, PDGF, or collagen III, can be included as part of the HP transcriptional cassette and result in high levels of expression of that protein from a human cell line.

Accordingly, the present invention also provides human gamma-IFN essentially free of other proteins of human origin. The invention further provides replicable expression vectors incorporating a DNA sequence encoding gamma-IFN and a self-replicating host cell system transfected thereby. The host system is mammalian cells.

The human gamma-IFN is produced by a process which comprises (a) preparing a replicable expression vector capable of expressing the DNA sequence encoding interferon in a suitable host cell system, (b) transforming said host system to obtain a recombinant host system, (c) selecting host cells containing the desired DNA plasmid vector, (d) maintaining said recombinant host system under conditions permitting expression of said interferon encoding DNA sequence to produce immune interferon protein, and (e) recovering said interferon protein. The interferon-encoding replicable expression vector is made by preparing a double-stranded complementary DNA (ds-cDNA) preparation representative of interferon mRNA, and incorporating the ds-cDNA into replicable expression vectors within a eukaryotic transcription cassette containing regulatory elements required for transcription of said cDNA. The preferred mode of recovering the interferon comprises reacting the proteins expressed by the recombinant host system with a reagent composition comprising at least one binding protein specific for interferon. Binding proteins, such as antibodies to gamma-IFN (either monoclonal or polyclonal), are used in the recovery step.

PREFERRED EMBODIMENTS

The invention provides an Epstein-Barr virus derived expression vector capable of replication in a prokaryotic host, as well as replication and expression of non-native genetic information in a mammalian host. This vector is comprised of a prokaryotic replicon, a eukaryotic replicon, and two transcriptional cassettes, each containing a transcriptional promoter and RNA processing signals. One eukaryotic transcriptional cassette is provided for expression of the dominant selectable marker (resistance to hygromycin), and the other cassette is used for expression of any desirable heterologous protein.

According to another embodiment, the invention provides a host transformed by an Epstein-Barr virus-derived expression vector capable of replication in a prokaryotic host, and replication and expression of non-native genetic information in a eukaryotic host. An example of a host cell line is African gree monkey kidney cells (ATCC designated cell line CCL 70). Other cell lines derived from a variety of tissues, i.e., human hepatoma cells, human lymphoid cells, human umbilical vein endothelial cells, human kidney cells, as well as cells derived from other species, i.e., monkey, dog, pig, etc., are also applicable. This invention, therefore, comprises a prokaryotic replicon, a eukaryotic replicon, a eukaryotic promoter, and at least two dominant selectable markers, and the process by which interferon, is produced from a replicable EBV expression vector. The presence of a signal sequence permits secretion of the gamma-IFN from the cell which facilitates subsequent recovery and purification of said protein from the conditioned culture medium.

DETAILED DESCRIPTION OF THE DRAWINGS

The EBV-derived vector, p220.2 (renamed p133 in FIG. 1), was a generous gift from B. Sugden, University of Wisconsin. It consists of plasmid p201 with the 43 bp SmaI-HaeIII fragment from pUC12 cloned into the unique NarI site of p201.

The intermediate cloning vector, p136, contains a transcriptional cassette for expression of human gamma-IFN cDNA. The transcriptional cassette contains (a) the mouse metallothione gene I (M-MT) promoter, from the KpnI site (approximately nucleotide −300) to the BglII site (approximately nucleotide +365) with the mRNA start site at nucleotide +301, (b) an 843 bp Sau3A fragment encoding human gamma-IFN joined to the M-MT promoter at the BglII site, and (c) SV40-derived RNA processing elements which consist of a fused fragment comprised of two noncontiguous regions of the SV40 genome. A 610 bp region (nucleotides 4710 to 4100 on the SV40 map) contains the small "t" intron (66 bp). This is fused to a 237 bp fragment (nucleotides 2770 to 2533 on the SV40 map) containing the polyadenylation signal at position 2586. This transcriptional cassette was released from p136 using a partial BglII cleavage followed by complete BamHI digestion. The 2.3 kb transcriptional cassette was purified and then cloned at the unique BamHI site of p220.2.

The resulting vectors, p147 and p162, are identical except for the orientation of the gamma-IFN-transcriptional cassette. In p147, the cassette is in the same transcriptional direction as the EBNA-1 gene, whereas, in p162 the cassette is oriented in the opposite direction of transcription. M.C.S.=multiple cloning site from pUC12 having the unique restriction enzyme recognition sites BamHI, XbaI, SalI and HindIII.

Transformation of E. coli K12 strain HB101 (ATCC No. 33694), screening of bacterial transformants, propagation of recombinant plasmids, and standard molecular biological manipulations were performed as described by Maniatis and Fritsch above.

FIGS. 1A and 1B. Expression of Human Gamma-IFN by CV-1 Cells Transformed by p147 and p162 DNAs CV-1 cells (ATCC designated cell line CCL 70) were transformed by p147 or p162 DNAs using the calcium phosphate co-precipitation transfection technique. Master cultures are defined as cultures in 100 mm plates which were allowed to become confluent during selection. In contrast, individual clones (FIG. 1B) were isolated from cultures seeded at low density in 100 mm plates to permit isolation of well separated clones after selection for hygromycin resistance.

Conditioned culture media from hygromycin resistant cells were tested for expression of human gamma-IFN using a biological assay which specifically measures a reduction in the cytopathic effect of encephalomyocarditis virus on human WISH cells, Braude, I. A. (1984) Biochemistry 23, 5603–5609.

(1A) Human gamma-IFN production by JY147 and JY162 cells from master cultures.

(1B) Human gamma-IFN production by cultures from JY147 and JY162 individual clones.

FIG. 2. Gradient SDS-Polyacrylamide Gel Electrophoresis (PAGE) of Human Gamma-IFN Protein Confluent cultures from NS72.4 (mouse cell line, C127, transformed by BPV/gamma-IFN vector), JY147.62, and JY147.64 (CV-1 cell lines transformed by EBV vectors) were labeled with $^{35}$S-methionine and immunoadsorbed with either normal goat sera (NGS) or goat-anti-human gamma-IFN sera, as described in Recombinant Methods.

Lanes A, C and E are conditioned culture media immunoadsorbed with NGS; and lanes B, D, and F are conditioned culture media immunoadsorbed with goat-anti-human gamma-IFN sera. Lanes A and B: JY147.62; Lanes C and D: JY147.64; Lanes E and F: NS72.4. Numbers to the right of the gel indicate molecular weights in kilodaltons (kD) of $^{14}$C-labeled high molecular weight range markers (Bethesda Research Laboratories).

PolyA selected RNA samples, each isolated from cells in three 150 mm plates, were analyzed by Northern blot hybridization as described in Recombinant Methods. The samples, from left to right, are: NS72.4 (described in legend FIG. 2), JY147.62, and JY147.64. Numbers to the right indicate the size of RNA markers shown in kilobase (kb) (Bethesda Research Laboratories). Both RNA samples, JY147.62 and JY147.64, comigrate with RNA derived from NS72.4 cells.

Total DNA was isolated from JY147.62, JY147.64, and JY147.69 CV-1 cells transformed by p147 DNA using the procedure of Gross-Bellard et al., Eur. J. Biochem., Vol. 36, p32–38 (1973) and 10 ug were reacted with restriction enzymes as recommended by the supplier (Bethesda Research Laboratories, New England Nuclear, International Biotechnologies, Inc., and Boehringer Mannheim). Fragments were separated by electrophoresis through 0.8% agarose (Bethesda Research Laboratories) in Tris acetate buffer (1X: 40 mM Tris, pH 7.8, 5 mM sodium acetate, 1 mM EDTA) at 22 volts for 16 hours. After electrophoresis, DNAs in gels were depurinated, denatured, and transferred to Gene Screen Plus (New England Nuclear), as described in the Recombinant Methods. Hybridization was performed for 16 hours, at 60° C., with $1 \times 10^7$ cpm of denatured, $^{32}$P labeled, human gamma-IFN cDNA probe (specific activity $4 \times 10^7$ cpm/ug). After hybridization, the blots were washed, air dried and exposed to XAR-5 film (Kodak) for 72 hours at −70° C. using one Dupont Lightning-Plus ™ intensifying screen.

(4A) Southern Analysis of p147 DNA Containing Cell Lines:

Plasmid or total cellular DNA was digested with restriction enzymes as indicated. Numbers to the left indicate sizes of human gamma-IFN specific sequences, and the positions of Forms I (supercoiled), II (nicked), and III (linear) DNAs. Numbers to the right show, location and size, in kilobases, of $^{32}$P-labeled mixed DNA marker fragments derived from lambda DNA digested with HindIII and phiX174 DNA digested with HaeIII.

(4B) Reconstruction Experiment to Quantitate the Number of Plasmid Copies Per Cell:

Serial dilutions of p147 plasmid DNA representing the indicated plasmid copies were used as standards. The number to the left indicates size of linear p147 DNA and numbers to the right are as described in FIG. 4A. Sample JY147.69 is estimated to contain 5 copies per cell.

DETAILED DESCRIPTION OF THE INVENTION

A. Definitions

As used herein, "interferon" denotes human immune gamma interferon (gamma-IFN) or its fragments, produced by cell or cell-free culture systems in biologically active forms having the capacity to affect cellular growth and viral replication, as does immune interferon native to human plasma.

Different alleles of interferon may exist in nature. These variations may be characterized by difference(s) in the nucleotide sequence of the structural gene coding for proteins of identical biological function. In addition, the location and degree of glycosylation, as well as other post-translation modifications may vary, and will depend, to a degree, upon the nature of the host and environment in which the protein is produced. It is possible to produce analogs having single or multiple amino acid substitutions, deletions, addition, or replacements. All such allelic variations, modifications, and analogs resulting in derivatives of interferon, which retain the biologically active properties of native interferon, are included within the scope of this invention.

"Expression vectors" refer to vectors which are capable of directing the expression of DNA sequences contained therein, where such sequences are linked to other regulatory sequences capable of effecting their expression. These expression vectors must replicate in the host organisms or cell culture systems either as episomes or bacteriophage, or as an integral part of the chromosomal DNA. The form of expression vector, which is used in the present invention, is Epstein-Barr virus (EBV) DNA.

"Shuttle vector" means the vector containing the necessary origins of replication (replicon) to allow replication in two distinct hosts. The shuttle vectors of this invention are capable of replication in E. coli, a prokaryotic organism, due to the presence of a bacterial replicon derived from plasmid pBR-delta, itself a derivative of plasmid pBR322 lacking sequences inhibitory to DNA replication in mammalian cells. These vectors are also capable of replication in an EBV susceptible eukaryotic cell line due to the presence of the EBV oriP and EBNA-1 genes.

Two regions of the EBV genome, oriP (nucleotides 7333 to 9516 on the EBV map) and EBNA-1 (nucleotides 107,567 to 110,176 on the EBV map) are required for the extrachromosomal replication of EBV-derived vector DNA. EBV plasmids containing these genetic elements are found exclusively as unintegrated extrachromosomal molecules at a number ranging from 1 to 90 in mammalian cells transfected with these vectors. Since integration of vector DNA does not occur, the physical integrity of the "passenger" DNA segment should be preserved.

"Recombinant host cells" refer to cells which have been transformed with vectors constructed and described herein using recombinant DNA techniques. As defined herein, gamma-IFN is produced as a consequence of this transformation. Gamma-IFN or its fragments produced by such cells are referred to as "recombinant immune interferon".

Size units for DNA and RNA are often abbreviated as follows: bp=base pair; kb=kilo (one thousand) base pair. For proteins we abbreviate: D=dalton; kD=kilodalton. Volumes are measured in ml=milliliters or ul=microliters, concentrations in ug/ml=micrograms/milliliter, molarity in M=molar or mM=millimolar. Temperatures are always given in degrees Celsius. Units of radioactivity for labels are in Ci=curies or mCi=millicuries with measurements in cpm=counts per minute.

B. Host Cell Cultures and Vectors

Recombinant vectors and methodology disclosed herein are suitable for use in host cells, covering a wide range of prokaryotic and eukaryotic organisms. In general, prokaryotes are preferred for the cloning and amplification of DNA sequences and in construction of vectors. For example, E. coli K12 strain HB101 (ATCC No. 33694) is particularly useful. Other microbial strains may be used. Vectors containing replication and control sequences which are derived from species compatible with the host cell are used in connection with these hosts. The vector ordinarily carries an origin of replication, as well as genetic characteristics capable of providing phenotypic selection in transfected cells. For example, E. coli can be transformed using the vector pBR322, which contains genes conferring resistance to ampicillin and tetracycline. These antibiotic resistance genes provide a means of identifying transformed cells.

The expression vector may also contain control elements which can be used by the vector for expression of its own proteins. Common prokaryotic control elements used for expression of foreign DNA sequence in E. coli include the promoters and regulatory sequences derived from the betagalactosidase and tryptophan (trp) operons of E. coli, as well as the pR and pL promoters of bacteriophage lambda. Combinations of these elements have also been used [e.g., tac, which is a fusion of the trp promoter (−35 region) with the lac promoter (−10 region) and the lac operator]. Other promoters have also been discovered and utilized, and details concerning their nucleotide sequences have been published enabling a skilled worker to combine and exploit them functionally.

In addition to microorganisms, cultures of cells derived from multicellular organisms may also be used as hosts. In principle, any such cell culture is workable, whether from a vertebrate or invertebrate source. However, interest has been increasing in vertebrate cells, and propagation of vertebrate cells in culture (tissue culture) has become a routine procedure in recent years. Examples of such useful hosts are the mouse C127 and L cells, monkey VERO, CV-1 and COS-1 cells, hamster CHO and BHK cells, and human 293, WI38, HeLa, 143 and 143EB cell lines. Expression vectors for such cells ordinarily include an origin of replication, a promoter located upstream of the gene to be expressed along with any RNA splice sites, a polyadenylation site, and a transcription termination sequence to convert the RNA transcripts into mRNA suitable for translation.

For use in mammalian cells, the control functions on the expression vectors are often provided by viral-derived sequences. For example, commonly used promoters are derived from retrovirus LTR regions, Adenovirus 2, Herpes virus tk gene and, most frequently, Simian Virus 40 (SV40). In addition, regulatory elements from cellular sources are also being used, i.e., the metallothionein promoter as described below. Further, it is also possible, and often desirable, to utilize promoter or control sequences naturally associated with the desired gene sequence, provided such control sequences are compatible with the host system. To increase the level of transcription, eukaryotic enhancer sequences can also be added to the construction. These sequences can be obtained from a variety of DNA viruses, such as SV40, polyoma, or oncogenic retroviruses, such as the mouse sarcoma virus and mammary tumor virus.

A mammalian origin of replication is usually part of the viral vector used as a vehicle, such as that provided by SV40, BPV, or other viral sources, or it may be provided by the host cell chromosomal replication mechanism. If the vector is integrated into the host cell chromosome, the latter is often sufficient.

The host cell is engineered to express a recombinant human gamma-IFN peptide, identical in its primary amino acid sequence to native human gamma-IFN isolated from induced peripheral blood lymphocytes. The protein is initiated with methionine, intracellularly processed, or cleaved extracellularly, giving rise to a mature peptide with an amino terminus identical to that of the native protein. Secretion is, presumably, effected by the signal sequence used herein, the natural gamma-IFN signal sequence.

C. Recombinant And Screening Methodology

The procedures below are but some of a wide variety of well-established procedures to produce specific reagents useful in the process of this invention. Double-stranded cDNA (ds-cDNA) is inserted into the expression vector by any one of many known techniques.

1. Construction of Recombinant Vectors

In general, the viral DNA vector is linearized by at least one restriction endonuclease, which will produce either two blunt or cohesive ends. The ds-cDNA is ligated with (or joined into) the vector at the cleavage site. Cleavage was performed by treating the DNA with restriction enzyme (or enzymes) in a suitable buffer. In general, about 1 ug of plasmid DNA or DNA fragments was used with about 1 unit of enzyme in about 20 ul of buffer solution for 1 hour. (Appropriate buffers and substrate amounts for particular restriction enzymes are specified by the manufacturer. Likewise, standard conditions for use of T4 ligase, T4 polynucleotide kinase and calf intestinal phosphatase are provided by the manufacturer.) Sticky end restriction enzyme fragments were modified to blunt ends, for example, by either fill-in repair using DNA polymerase Klenow fragment or S1 nuclease digestion of the single stranded DNA. After incubations, protein was removed by extraction with phenol and chloroform, and the nucleic acid was recovered from the aqueous fraction by precipitation with ethanol.

2. Introduction of Recombinant DNA into Bacterial or Mammalian Cells

If prokaryotic cells or other cells which contain substantial cell wall material are employed, the most common method of transformation with the expression vector is calcium chloride pretreatment to render the cells competent for DNA uptake. If cells without cell wall barriers are used as host cells, transfection is carried out by the calcium phosphate coprecipitation method, and as described below.

All incubations, unless otherwise noted, were maintained at 37° C. in 5% $CO_2$/95% air. A 2X solution [2X: 1 mM tris-(hydroxymethyl) aminomethane (Tris), pH 7.9, 0.1 mM ethylenediaminetetraacetate (EDTA), 250 mM $CaCl_2$] was added to the recombinant DNA; the combined solution was then added to an equal volume of 2X HBS solution (1X: 140 mM NaCl, 25 mM HEPES [N-2-hydroxyethylpiperazine-N'-2-ethanesulfonic acid] 0.75 mM sodium phosphate, pH 7.1) resulting in a final DNA concentration of 30 ug/ml. The DNA precipitate was allowed to form at room temperature over a 45-minute period. Portions representing 10 ug of the recombinant DNA were added to cell cultures at 90% confluency in 60 mm Petri dishes (Falcon) containing 2 ml of fresh Dulbecco's modified Eagle's medium (DMEM), and incubation was continued at 37° C. for 4 hours. Then the medium was changed, and the monolayers were washed 1X with DMEM followed by treatment with 1 ml of 15% glycerol in HBS for 2 minutes at room temperature. The monolayers were washed 3X at room temperature with DMEM; then fresh maintenance medium [DMEM+10% fetal bovine serum (FBS)] was added.

In some experiments, cells were incubated in DMEM+10% FBS with 5 mM sodium butyrate (final) for $16 \geq 24$ hours to increase the transcriptional efficiency of plasmid DNA, followed by incubation in maintenance medium. Four days after transfection, confluent cells in 60 mm plates were split at a ratio of 1:5, 1:10, or 1:50 into 100 mm plates, and placed under selection in DMEM+10% FBS with the antibiotic hygromycin-B (Calbiochem) at a concentration of 200 ug/ml. After 2 to 4 weeks, depending on the cell line, non-transformed cells had been killed and viable colonies of resistant cells could be transferred to 12-well cloning plates (COSTAR).

Other methods for introducing DNA into cells such as nuclear injection or protoplast fusion can also be used. Following transfection, the host cells are cultured in selective media, and foreign proteins encoded by the foreign DNA insert are produced.

3. Analysis of Gamma-IFN Specific Peptide

In order to visualize the human gamma-IFN expressed and secreted by CV-1 cells containing plasmid p147 DNA, cell conditioned media were incubated with human gamma-IFN antisera to concentrate the protein which was then analyzed by SDS-PAGE. Confluent cultures from NS72.4 (a C127 human gamma-IFN-producing BPV vector transformed line, described in FIG. 2), JY147.62 and JY147.64 (CV-1 cell lines transformed by EBV vectors) in 100 mm plates were rinsed 2X with methionine-free DMEM with 2% dialyzed fetal calf serum (Gibco) and incubated in 3 ml of this medium for 60 minutes at 37° C. Cells were labeled with 0.5 mCi of $^{35}S$-methionine per plate (1097 Ci/mmole; New England Nuclear) for 4 hours at 37° C. Conditioned culture media were then clarified at 1000 xg for 10 minutes. To minimize protein degradation by proteases in the sample, NONIDET P-40 TM (NP40) (Shell) was added to a final concentration of 1%, and phenylmethylsulfonyl fluoride was added to a final concentration of 200 ug/ml (Boehringer Mannheim). For immunoadsorption, duplicate aliquots of 500 ul each were first precleared with 4 ul of normal goat sera (NGS) for 1 hours at 4° C. Bound proteins were removed with 30 ul of a 10% (weight/volume) suspension of Protein A Sepharose beads (Pharmacia) for 30 minutes at 4° C., followed by a 10,000 xg, 30 second centrifugation (Eppendorf). Cleared supernatants were incubated with either NGS (5 ul) or goat-anti-human gamma-IFN sera (5 ul) overnight. Bound proteins were concentrated by incubation with 40 ul of a 10% (weight/volume) suspension of Protein A Sepharose beads for 1-2 hours followed by centrifugation as above. After rinsing, (3X with 500 ul of a solution containing 1% NP40, 0.5% SDS, 100 mM Tris, pH 7.4, and 150 mM NaCl) the beads were resuspended in 2X Laemmli buffer (2X: 0.2M Tris, pH 6.8, 6% SDS, 30% glycerol, 0.02M beta-mercaptoethanol, and 0.01% bromophenol blue), boiled for 3 minutes and centrifuged as described above. The supernatants were kept on ice until analyzed by SDS gradient-polyacrylamide gel electrophoresis (PAGE). After electrophoresis, the gels were fixed for 60 minutes in a solution containing 30% methanol and 10% glacial acetic acid, treated with En$^3$Hance TM (New England Nuclear) for 30 minutes, dried, and exposed to XAR-5 film (Kodak) at room temperature.

4. Southern Analysis of Cellular DNA

Total cellular DNA, isolated from cell pellets by the procedure disclosed in *Eur. J. Biochem* (1973) Vol. 36, p32-38, was subjected to electrophoresis in 0.8% agarose gels by standard methods. The immobilized DNA in the gels was depurinated with acid by soaking the gel for 30 minutes in 0.2M HCl, denatured with alkali by soaking for 30-60 minutes in 0.5M NaOH/1.5M NaCl, and neutralized in 1M ammonium acetate/0.02M NaOH. The DNA was transferred "bidirectionally" to Gene Screen TM (New England Nuclear), fixed to the membrane by baking (80° C. in vacuo), then hybridized following established methods.

5. RNA Analysis a. RNA Isolation

Prior to the selection of RNA, all solutions were autoclaved or filter sterilized and treated with diethylpyrocarbonate (DEP). Total RNA was isolated by the method disclosed in Biochemistry, Vol. 18, p5294-5299 (1979), followed by electrophoresis in agarose slab gels for "Northern" blot hybridization. Alternatively, to isolate polyA containing RNA, confluent cells were washed 2X in phosphate buffered saline (PBS), scraped into a 50 ml conical tube and centrifuged at 1000 xg for 5 minutes. Cell pellets were lysed in 25 ml of a solution containing 0.5% SDS, 100 mM NaCl, 20 mM Tris, pH 7.4, and 1 mM EDTA. Proteinase K was added to a concentration of 200 ug/ml. DNA was sheared by passing the solution through a 22 gauge needle. The sample was then incubated at 37° C. for 60 minutes. An oligo d(T) cellulose suspension was prepared in water and then adjusted to 200 mM NaOH. Following five washes in high salt buffer (HSB) consisting of 400 mM NaCl, 1 mM EDTA, and 0.1% SDS, the resin was collected and resuspended in an equal volume of HSB. One ml of the resin was added to the RNA solution, the mixture was placed in a 150 cm$^2$ flask and incubated on a rotating platform for 60 minutes at room temperature. The suspension was collected by centrifugation [10,000 xg, 30 seconds (Eppendorf)], washed 4 times with HSB, poured into a disposable column (BioRad), and washed again with HSB with 5X the volume. PolyA containing RNA was eluted with a 0.5 ml aliquot of low salt buffer (LSB) (10 mM Tris, pH 7.4, 1 mM EDTA and 0.1% SDS). This was followed by 2 additional 0.5 ml aliquot elutions, after which the 3 fractions were pooled; Na acetate (0.3M final concentration) was then added, and RNA was precipitated with 2.5 volumes of ethanol. RNA precipitates were collected by centrifugation [10,000 rpm (Beckman JS-13) for 30 minutes at 0° C.]. PolyA RNA concentrations were determined by spectrophotometric readings at 260 wavelength.

b. Gel Electrophoresis

For analysis, the RNA was denatured in 2.2M formaldehyde and 50% formamide, and fractionated by electrophoresis in a 1.25% agarose gel containing 2.2M formaldehyde. A separate lane was included containing DNA molecular weight standards, prepared by digesting lambda DNA with HindIII and phiX174 DNA with TaqI and end labeling with $^{32}$P or RNA molecular weight standards (Bethesda Research Laboratories). The buffer for running the formaldehyde gel was 20 mM MOPS (3-(N-Morpholino) propane sulfonic acid), 5 mM sodium acetate, and 1 mM EDTA. After electrophoresis, the gel was soaked for 30 minutes in 50 mM NaOH/10 mM NaCl, and neutralized in 0.1M Tris, pH 7.5 (30 minutes). The RNA was then transferred to nitrocellulose (Schleicher and Schuell) by blotting with 10X SSC (1X:0.150M NaCl, 0.045M Na citrate, pH 7.0). The blot was baked at 80° C. under vacuum for 2 hours and stored.

c. Hybridization

Filters were prehybridized for 2.5 hours at 42° C. in 50% formamide, 5X SSC (5X:0.75M NaCl, 0.225M Na citrate, pH 7.0), and 10X Denhardt's solution (10X: 0.2% ficoll, 0.2% polyvinylpyrrolidone, 0.2% bovine serum albumin), 100 ug/ml herring sperm DNA, 100 ug/ml tRNA, 0.2% SDS and 20 mM sodium phosphate, pH 6.5. Hybridization using $1 \times 10^7$ cpm of $^{32}$P-labeled human gamma-IFN cDNA probe ($4 \times 10^7$ cpm/ug) was performed for 16 hours at 42° C. in the prehybridization buffer. Filters were washed 2X with 100 ml of 2X SSC for 5 minutes at room temperature followed by 2 washes (200 ml each) with 2X SSC/1.0% SDS for 30 minutes at 60° C. After 2 additional washes with 100 ml 0.1 X SSC for 30 minutes at room temperature, the filters were air dried and then exposed for 16 hours at −70° C. using Kodak XAR-5 film and one Dupont Lightning-Plus TM intensifying screen.

d. Preparation of $^{32}$P-Labeled Probes

Nick translation reactions were performed according to the method disclosed in *J. Mol. Biol.* (1977) Vol. 113, p237-251, using 1 ug of cDNA in a reaction volume of 50 ul. The reaction mixture, assembled at 0° C., contained the 1X nick-translation buffer (50 mM Tris pH 7.2, 10 mM MgSO$_4$, 0.1 mM dithiothreitol, 50 ug/ml bovine serum albumin), 0.1 mM each of unlabeled dATP, dGTP, dTTP, 100 pmoles $^{32}$P-dCTP (specific activity=1 mCi/.0012 uM) New England Nuclear), $5 \times 10^{-5}$ ug DNase I, and 10 units of *E. coli* DNA polymerase I (Boehringer Mannheim). The reaction was incubated at 16° C. for 60 minutes, then stopped by adding 1 ul of 0.5M EDTA. The cDNA was separated from the unincorporated deoxynucleotide-triphosphates by chromatography on a Sephadex G-50 column [Worthington mini-spin column (Cooper Biomedical)]following the manufacturer's method. The $^{32}$P-labeled DNA had a specific activity in excess of $10^7$ cpm/ug.

6. Biological Assay

Clones containing the entire gene for immune interferon, or parts thereof, were identified in a semi-micro cytopathic effect (C.P.E.) inhibition assay by the Quality Control Division (Meloy Laboratories) using human WISH cells as the indicator cells and encephalomyocarditis virus (EMC) as the challenge virus. This method of identification requires that the ds-cDNA for human gamma-IFN be inserted into a vector containing appropriate regulatory nucleic acid sequences adjacent to the insertion site. These regulatory sequences initiate transcription, and subsequently, translation of the ds-cDNA molecule inserted in the vector.

Those clones containing interferon cDNA sequences correctly positioned, relative to the regulatory sequences, transcribed and translated the gamma-IFN. Restriction endonuclease digestion and nucleotide sequencing techniques were used to determine the nucleic acid sequence of the cDNA fragments. The sequence was then used to predict the primary amino acid sequence encoded by the cDNA insert. Correct translation was verified by physical means (i.e., mobility on SDS-PAGE, immunoadsorption, and neutralization), and occasionally by partial amino acid sequencing of the recombinant peptide.

EXAMPLE

Isolation Of The Gamma-IFN Sequences And Gene Regulatory Sequences

The gamma-IFN cDNA clone employed in this invention has been described in detail in copending application U.S. Ser. No. 720,092 filed, Apr. 5, 1985. Briefly, size fractionated mRNA was isolated from human peripheral blood lymphocytes that had been induced with A23187 and mezzarine. The mRNA was converted into ds-cDNA and cloned into the PstI site of pBR322 by G-C tailing using standard procedures. An 843 bp Sau3A fragment containing the gamma-IFN signal peptide, coding region, and translation termination codon, was cloned into a pBR322 derivative. The resulting construct contained gamma-IFN sequences placed downstream from a mouse metallothionein gene I promoter, and also contained the SV40 small "t" antigen splice sites and polyadenylation signal. An additional construction also contained the Moloney murine sarcoma virus (M-MSV) enhancer sequences 5' of the mouse metallothionein promoter.

Construction Of The EBV/Gamma-IFN Expression Vector

The vector (p133) described below, containing the EBV-derived genetic elements, PBR322 sequences, and the hygromycin phosphotransferase (hph) expression cassette was a generous gift of B. Sugden (University of Wisconsin), and is designated as p201 when described in Nature, Vol. 313, p812-815 (1985) or, when containing the pUC12 derived multiple cloning site, as p220.2. The gamma-IFN cDNA insert (843 bp) and regulatory elements, described above, were ligated to an EBV replicon containing the following elements: (1) EBV-derived sequences which permit stable extrachromosomal replication of the vector in a variety of cell lines, (2) a multiple cloning site from pUC12 consisting of unique recognition sites for 4 restriction enzymes [BamHI, XbaI, SalI, and HindIII], (3) a transcriptional cassette consisting of regulatory sequences and the hygromycin-B gene to facilitate dominant selection of mammalian cells harboring the EBV replicon, and (4) pBR322 sequences deleted of the "poison sequences" and comprising a bacterial origin of replication and the betalactamase gene. The details of the EBV-gamma-IFN expression vector construction are described below, beginning with the EBV sequences.

EBV Sequences: The EBNA-1 gene (nucleotides 107,567 to 110,176 on the EBV map) is delineated on the 5' end with a BamHI site that was made blunt with DNA polymerase and with a PvuII site (naturally blunt) on the 3' end. The product of the EBNA-1 gene is a DNA-binding protein which binds to oriP and is required for the maintenance of the EBV replicon as an extrachromosomally replicating DNA molecule.

Ligation of the PvuII site of EBNA-1 to a previously blunted SphI site of the oriP sequence (nucleotides 7333 to 9516 on the EBV map) joins oriP DNA to the EBNA-1 sequence.

Hygromycin-B$^r$ Cassette And Multiple Cloning Site: The SstII site at the 3' end of oriP and the BstEII site of the Herpes simplex virus (HSV) type I thymidine kinase (tk) termination sequence (625 bp) were each blunted and then joined by a blunt end ligation. The 43 bp polylinker from pUC12 encompassing the region between the SmaI and HaeIII recognition sites, is shown below.

This sequence was inserted at the NarI site of the HSV tk termination sequences using blunt-end ligation. The hph gene which confers resistance to the antibiotic hygromycin-B was inserted between the BglII and SmaI sites of the HSV termination sequences and promoter regions. The 5' end of the hph gene was ligated to a 250 bp PvuII/BglII DNA fragment containing the HSV tk promoter.

The remaining sequences are derived from pBR322, pBR-delta. The HindIII site at the 5' end of pBR322 sequences was joined to the BamHI site at the 5' end of the EBNA-1 sequences. The 3' end of the pBR322 sequences was ligated to the PvuII site at the 5' end of the HSV tk promoter. This vector containing the above described EBV-derived genetic elements, PBR322 sequences, and the hph expression cassette, is described as p201, or as p220.2 containing the pUC12 derived multiple cloning site.

Gamma-IFN Sequences Cassette

The gamma-IFN sequences, including the gamma-IFN signal peptide, coding region, and translation termination codon, were isolated from p136.5 or p72.4 using a complete BamHI and a partial BglII restriction enzyme digestion and inserted into the unique BamHI site in the multiple cloning region of the plasmid described above. A BamHI site is retained at the 3' end of the cassette, and a non-functional BamHI/BglII hybrid site is generated at the 5' end (p147, p162, and p185). The transcriptional cassette, containing the human cytomegalovirus (HCMV) enhancer, SV40 promoter, gamma-IFN cDNA, and SV40 polyadenylation and splice signal sequences, was released from p212 by a complete BamHI digest and cloned into the BamHI site of p133 resulting in plasmids p222 and p223. For plasmids p239 and p240, which contain the M-MSV enhancer, M-MT promoter, gamma-IFN cDNA, and the same RNA processing sequences as described above, a transcriptional cassette containing these element was released from plasmid p206 by a complete BamHI digest and cloned into the BamHI site of p133.

M-MT Promoter: The mouse metallothionein gene I promoter is the KpnI [approximately (−)300 bp] to BglII[(+)365 bp] fragment with the CAP site (mRNA start site) at (+)301 bp. Since the coding region of the M-MT gene begins downstream (at +374 bp) from the 3′ end (position +365 bp) of the promoter described herein, no fusion products result. The M-MT promoter is placed in EBV-derived plasmids identified as p185, p239, p240, as well as p147 and p162. Vectors p147 and p162 are derived from p136 and lack the MSV enhancer element.

M-MSV Enhancer: Enhancers are cis acting genetic elements which increase the level of transcription when present in either orientation, often exerting their effect at distances well over 1 kb from the gene being expressed. The Moloney murine sarcoma virus (M-MSV) enhancer fragment has a broad host range and has been shown to efficiently increase expression of recombinant DNAs from BPV vectors in mouse cells. The M-MSV enhancer fragment extends from the HinfI (base 141) to the XbaI (base 525) site in the proviral long terminal repeat. Both sites were converted to BamHI sites with synthetic linkers to facilitate cloning. The M-MSV enhancer is found in constructions p185, p239, and p240.

Gamma-IFN: Complete details of the isolation of the gamma-IFN cDNA are described above. The Sau3A gamma-IFN DNA insert is joined to the mouse metallothionein gene I promoter at the BglII site. The 3′ end of the gamma-IFN sequences is joined to the SV40 RNA processing elements.

SV40 Poly-Adenylation Site: The SV40-derived RNA processing elements consist of a fused fragment comprised of two noncontiguous regions of the SV40 genome. A 610 base pair region (nucleotides 4710 to 4100 on the SV40 map) contains an intron (66 bp) from the early region of the viral genome. This is fused to a 237 bp fragment (nucleotides 2770 to 2533 on the SV40 map) containing the polyadenylation signal at position 2586. The 5′ BglII site is joined to the Sau3A site at the 3′ end of gamma-IFN cDNA. The BamHI site at the 3′ end is ligated to the BamHI site within the multiple cloning sequence derived from pUC12.

Additional Regulatory Elements: Other promoter and enhancer elements were tested to obtain greater levels of gene expression. One example is the HCMV enhancer reported to enhance high levels of gene expression in a variety of cell types when in combination with the SV40 early promoter. Vectors p222 and p223 contain this combined regulatory unit derived from plasmid p198-1.

The 198-1 vector comprises a pML2 sequence and a eukaryotic transcriptional cassette, consisting of the following regulatory elements described in a 5′- 3′ direction (i) an enhancer element derived from the HCMV DNA, encompassing a 262 bp fragment extending from nucleotide −524 to nucleotide −263 upstream of the transcriptional initiation site of the major immediate-early gene, (ii) a 144 bp fragment encompassing the early promoter region of SV40 (nucleotides 72 to 5172 on the SV40 map [SV40 DNA is 5242 bp long]), and (iii) RNA processing elements. This region contains the small "t" intron and early polyadenylation signal derived from SV40 DNA. The HCMV enhancer/SV40 early promoter fragment was generously provided by W. Schaffner (Zurich, Switzerland) and is described in Cell, Vol. 41, p521-530 (1985).

Expression of Gamma-IFN In Mammalian Cells

A variety of cell lines were examined to determine their comparable ability to support replication of plasmid DNA and to allow high-level expression of gamma-IFN from the EBV vectors. The cell line of choice was CV-1, African green monkey kidney (ATCC designated cell line CCL 70). All cells were maintained in Dulbecco's modified Eagle medium (Meloy Laboratories, Springfield, VA) supplemented with 10% heat-inactivated fetal calf serum (GIBCO), penicillin (10 U/ml), and streptomycin (100 ug/ml). DNA transformation was performed by using the calcium phosphate co-precipitation method followed by glycerol enhancement as described under Recombinant and Screening Methodology.

Figure 1:
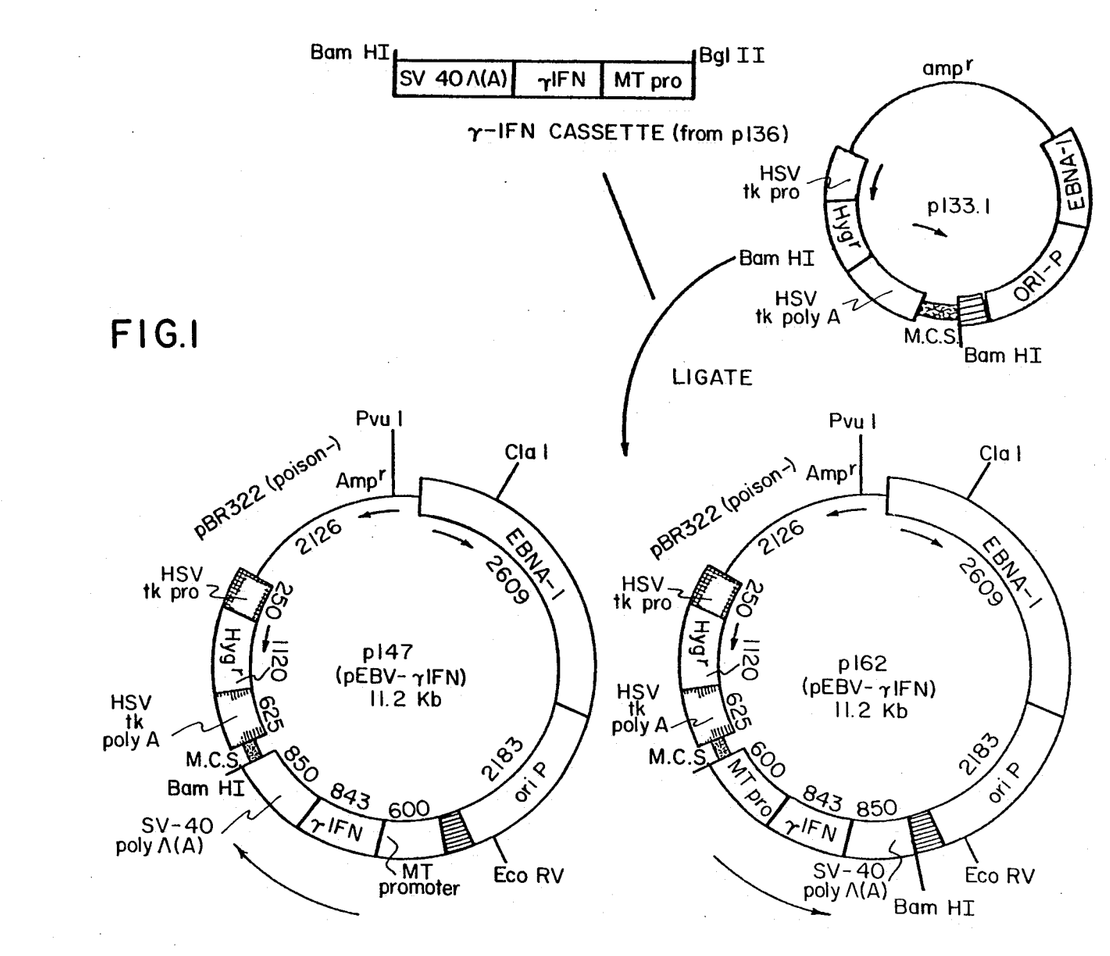
FIG. 1. Strategy of Vector Constructions
Figure 1A:
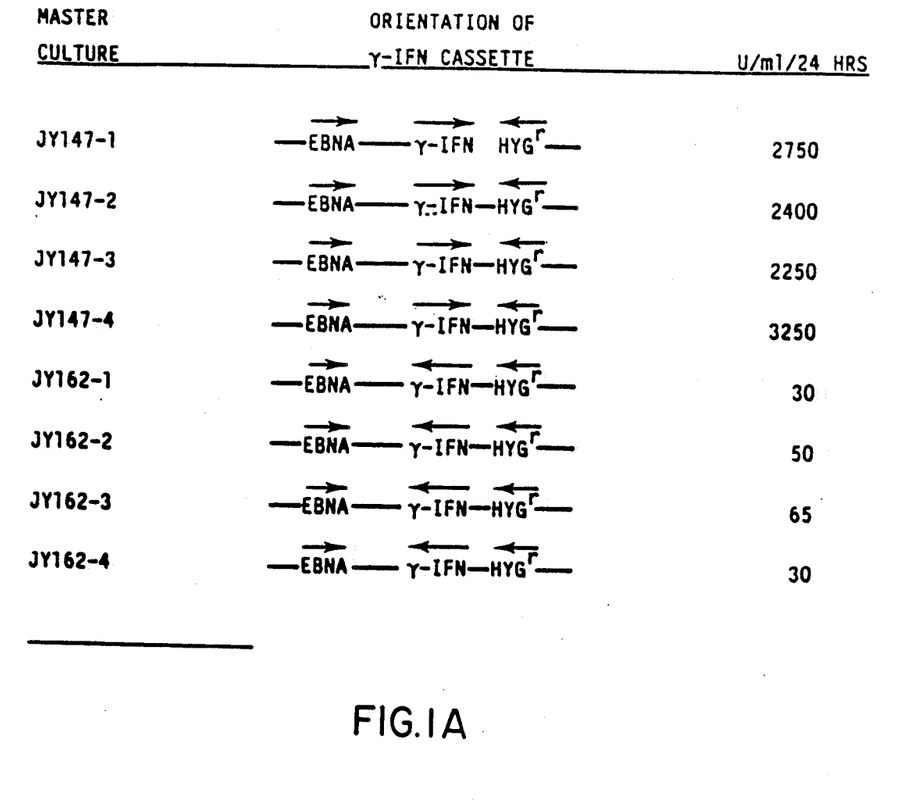
Figure 1B:
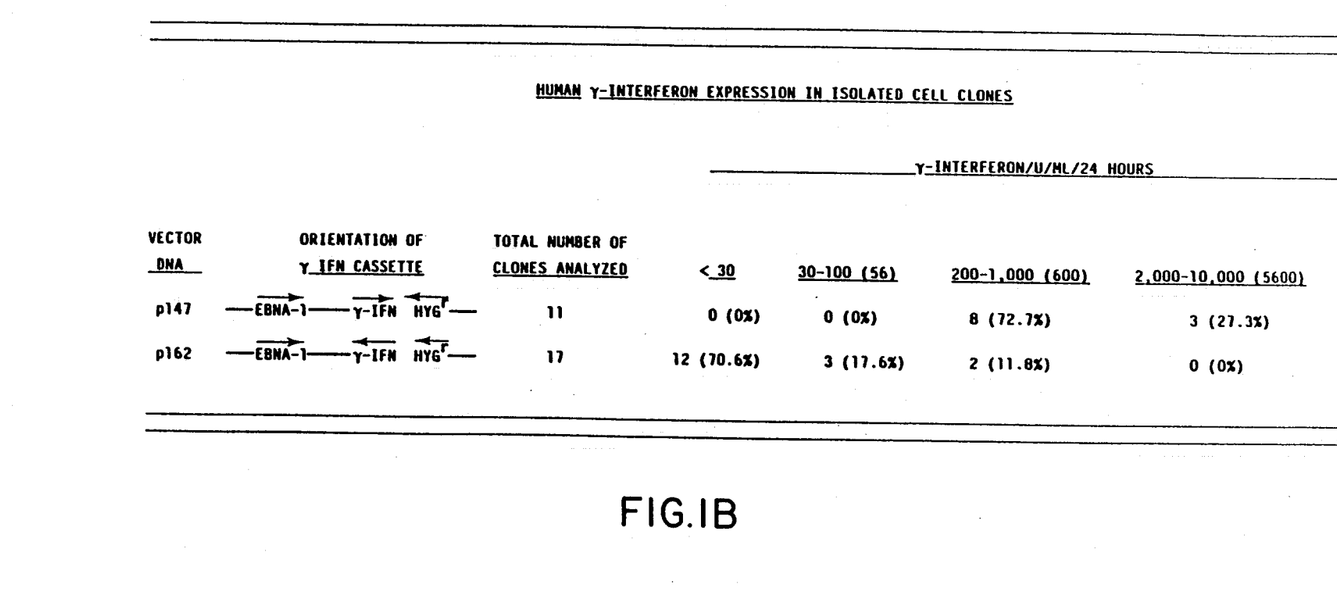

Expression of the gamma-IFN protein was initially determined by a bioassay for gamma-IFN. The biological assay specifically measures a reduction in the cytopathic effect of EMC virus on human WISH cells. The results demonstrate the levels of gamma-IFN, activity as well as the variation in the amount of biologically active gamma-IFN produced by CV-1 master cultures (FIG. 1A) and individual clones (FIG. 1B) transformed by different EBV recombinant vectors.

Figure 2:
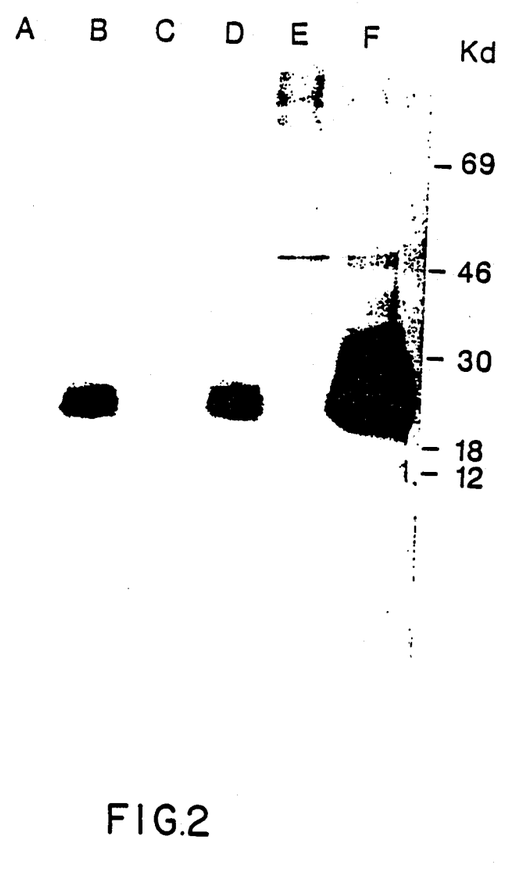

Having identified gamma-IFN biological activity in EBV transformed cells, the nature of the polypeptide produced was investigated. Cells lines (JY147.62, JY147.64 and JY147.69) were labeled with $^{35}$S-methionine, extracellular media was harvested, and gamma-IFN immunoadsorbed with a polyclonal goat anti-gamma-IFN serum. The immunoadsorbed proteins were then analyzed on SDS-polyacrylamide gels, as described above. Analysis of CV-1 cells transformed with pEBV-gamma-147 demonstrated the presence of a prominent band at a molecular weight of 22,000 to 25,000 daltons, which is identical in its electrophoretic mobility to native human gamma-IFN, as well as to recombinant human gamma-IFN produced using the BPV vector system (FIG. 2). This band was absent from the media obtained from non-transformed cells (data not shown). The primary amino acid sequence of gamma-IFN comprises a peptide of 18,000 daltons. After glycosylation, the apparent molecular weight is increased to 22,000 to 26,000 daltons. The observation that recombinant gamma-IFN, produced using the EBV vector system, has the expected molecular weight as glycosylated gamma-IFN, strongly suggests that the protein is properly modified.

Figure 3:
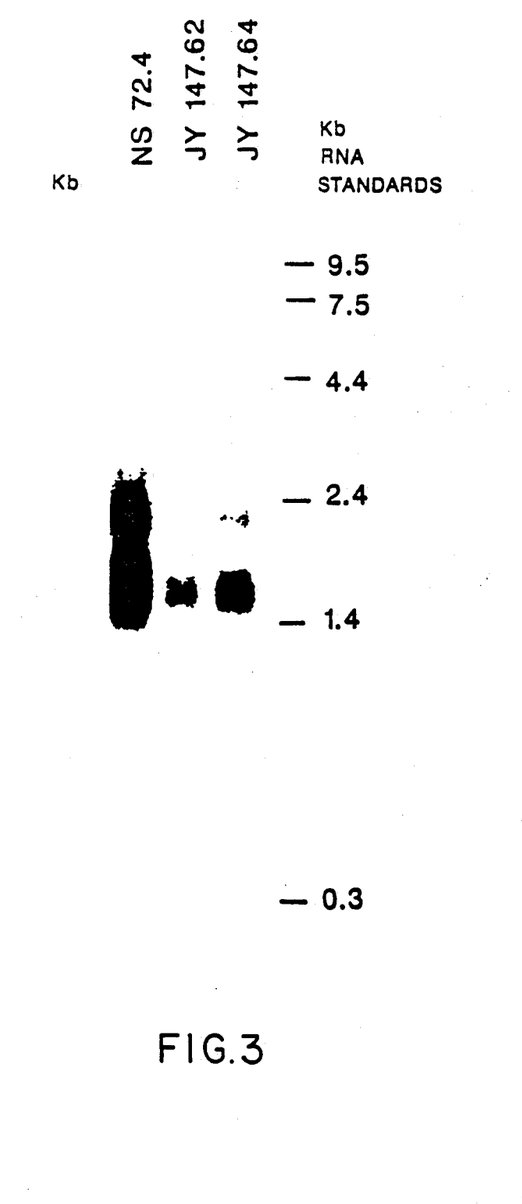
FIG. 3. Northern Analysis of Gamma-IFN Specific PolyA Selected RNA

The relative amounts and sizes of the transcripts of human gamma-IFN-specific RNA from CV-1 cells harboring the recombinant DNA were examined by Northern analysis. Poly A containing RNA was extracted, as described in Recombinant and Screening Methodology, separated by agarose-formaldehyde gel electrophoresis and transferred to nitrocellulose filter paper (Schleicher & Schuell). Filters were hybridized to $^{32}$P labeled human gamma-IFN DNA probe. After washing, the transcripts were visualized by autoradiography. As seen in FIG. 3, gamma-IFN/EBV transfected cells contain two gamma-IFN-specific RNA hybridizing bands corresponding to 1400 and 2000 bases. Transcripts of the same size are also seen in C127 cells harboring gamma-IFN/BPV vectors.

Figure 4A:
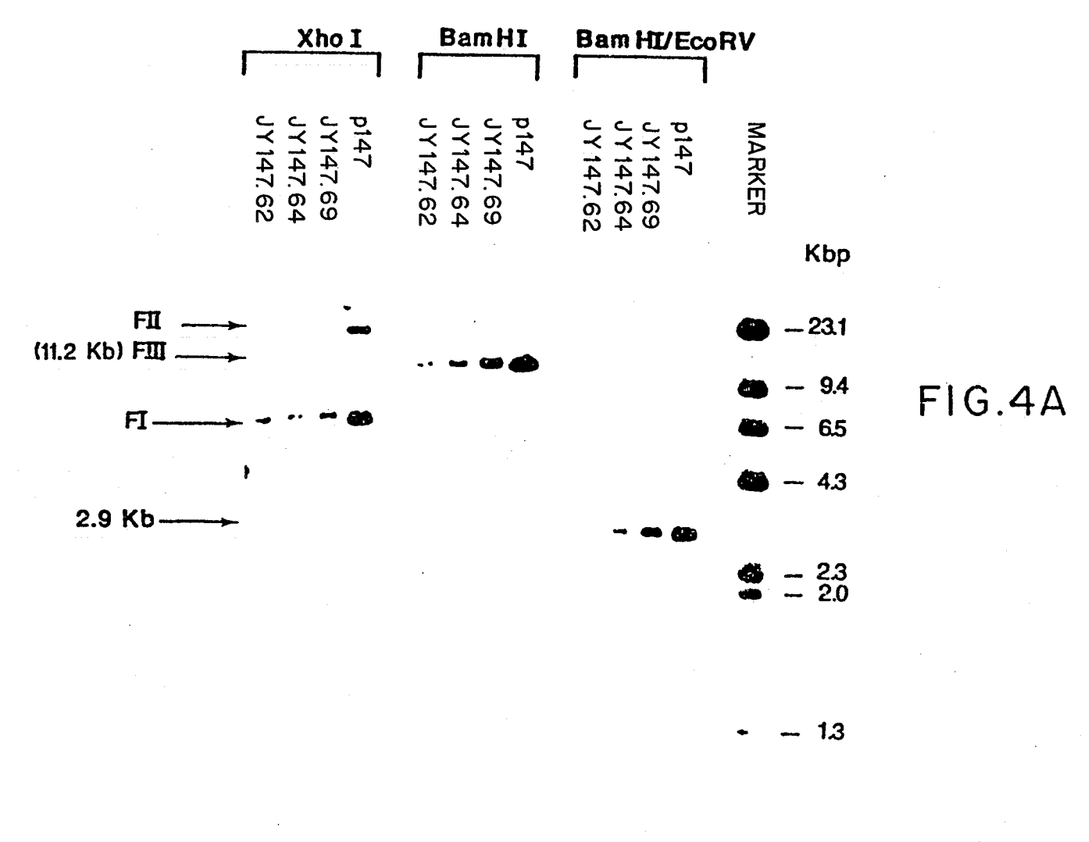
FIGS. 4A and 4B. Southern Analysis of Human Gamma-IFN Specific DNA

To determine whether the gamma-IFN/EBV plasmids were present as extrachromosomal molecules, or whether they had integrated into host cell DNA, Southern analysis was performed. Total cellular DNA was isolated, digested with several restriction enzymes, and analyzed by Southern transfer and hybridization. Analysis with XhoI (a no cut enzyme) or BamHI (a single cut enzyme) show the presence of a single gamma-IFN-specific band comigrating with supercoiled or linear parental plasmid DNA, respectively (FIG. 4A). Co-digestion with BamHI and EcoRV, which releases a 2.9 kb fragment containing the metallothionein promoter, human gamma-IFN sequences, and the SV40 polyadenylation sequence demonstrates the absence of detectable deletions or rearrangements in DNA from CV-1 cells transfected with p147 DNA. Thus, the EBV-derived plasmids exist as non-integrated, extrachromosomally replicating DNA molecules in the CV-1 host cell.

Figure 4B:
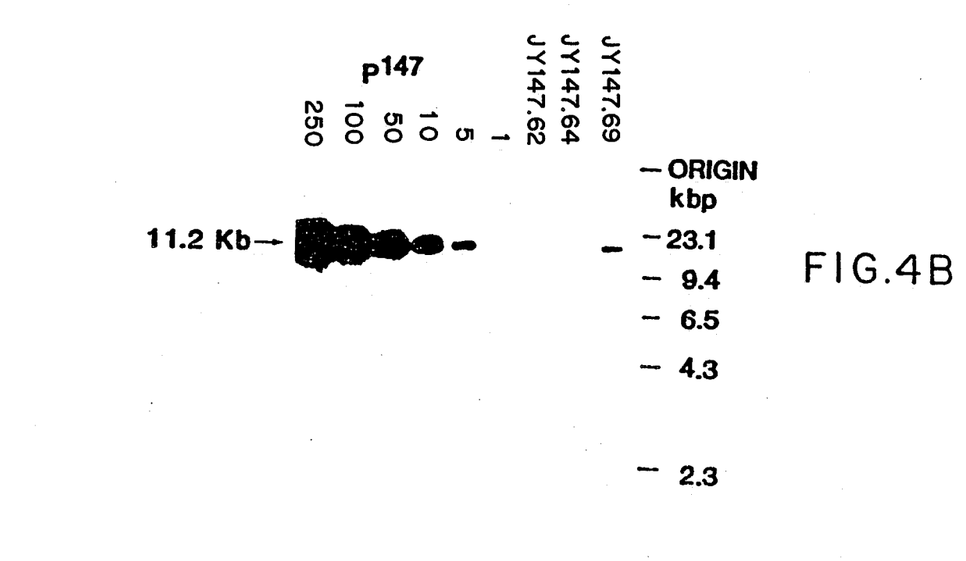

To quantitate the number of resident plasmid copies per cell, DNA from JY147 cells was digested with BamHI and electrophoresed adjacent to BamHI-digested plasmide p147 DNA. The latter was applied to the gel at concentrations corresponding to plasmid copies ranging from 1 to 250 per cell (FIG. 4B). Such analysis demonstrates that the resident plasmid is present as an autonomously replicating DNA molecule at a copy number ranging from 1 to 5 copies per cell.

p222 (pEBY-Gamma-IFN)

Although cells transfected by plasmid p147 DNA, expressed and secreted human gamma, the plasmid DNA was modified to achieve higher expression levels. The EBV shuttle vector p222 is identical to p147 except for the replacement of the mouse metallothionein I gene (M-MT) promoter of p147 with the human cytomegalovirus (HCMV) enhancer and the SV40 early promoter. This was achieved through the construction of an intermediate vector, p198-1.

The 198-1 vector comprises the pML2 sequence described in *Papillomaviruses: Molecular and Clinical Aspects* (1985), p515–527 and a eukaryotic transcriptional cassette, consisting of the following regulatory elements described in a 5'- 3' direction: (i) an enhancer element derived from the HCMV DNA, encompassing a 262 bp fragment extending from nucleotide −524 to nucleotide −263 upstream of the transcriptional initiation site of the major immediate-early gene, (ii) a 144 bp fragment encompassing the early promoter region of SV40 (nucleotides 72 to 5172 on the SV40 map [SV40 DNA is 5242 bp long]), and (iii) RNA processing elements. This region contains the small "t" intron and early polyadenylation signal derived from SV40 DNA. The HCMV enhancer/SV40 early promoter fragment was generously provided by W. Schaffner (Zurich, Switzerland) and is described in *Cell* 41, 521–530 (1985).

Figure 5:
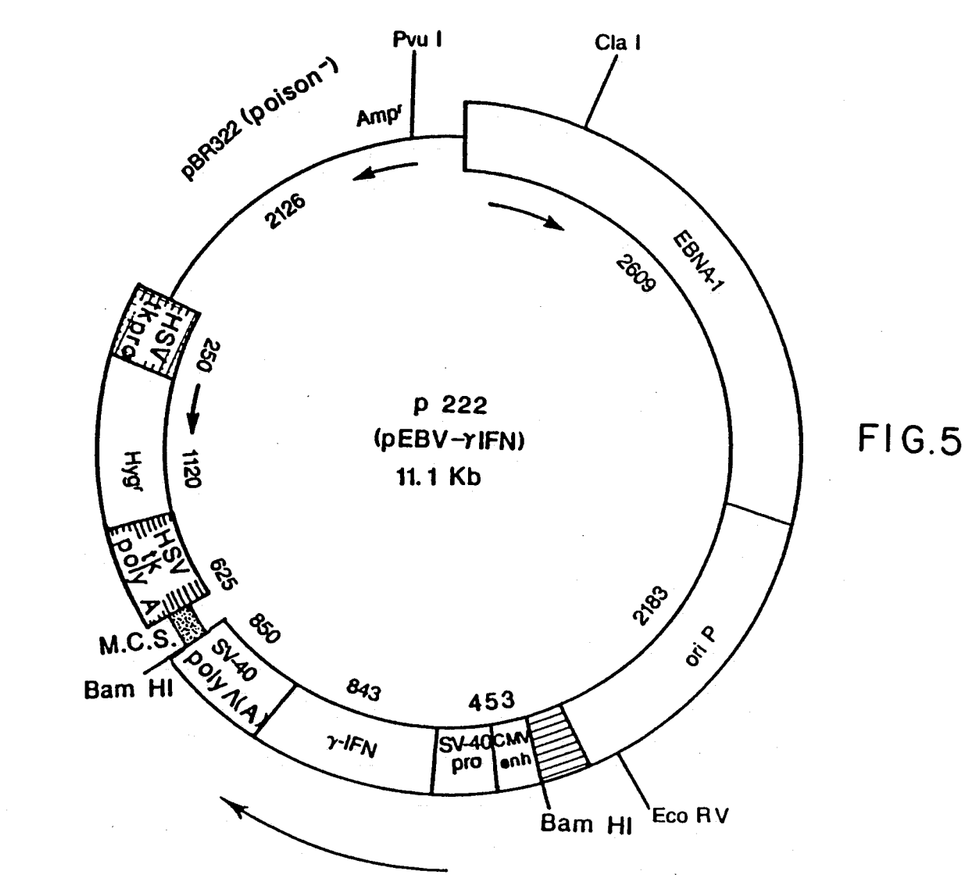
FIG. 5 and FIG. 6. Construction of Human-Gamma-IFN Vectors, p222 and p239
Figure 6:
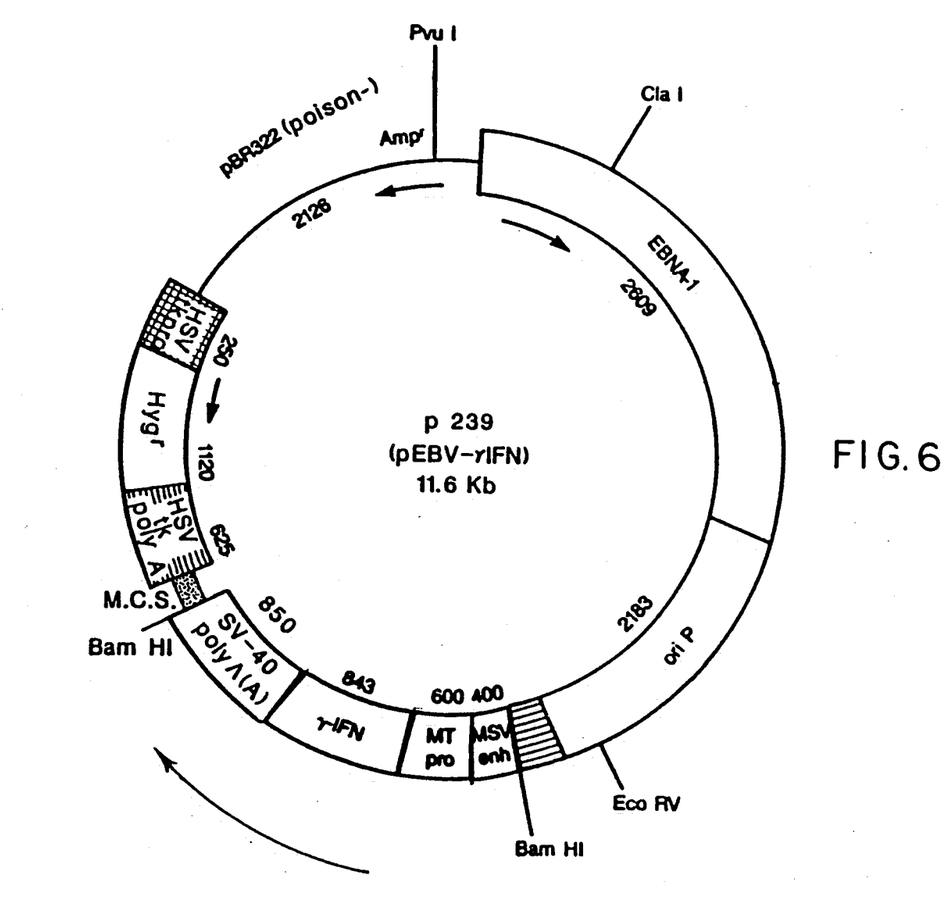

A human gamma-IFN cDNA as an 843 bp Sau 3A fragment was inserted at the unique BglII site of p198-1 to produce p212. The unique SmaI site of p212 was then converted to a BamHI site using a commercially purchased oligonucleotide (Bethesda Research Laboratories) to produce plasmid p213. To construct the final EBV vector, p222 (shown in FIG. 5), the transcriptional cassette consisting of the HCMV enhancer, SV40 early promoter, gamma-IFN cDNA, and SV40 RNA processing elements, was removed from p213 using BamHI and ligated into the EBV vector p133 at the unique BamHI site.

Plasmid p222 DNA was introduced into CV-1 cells using calcium phosphate co-precipitation, followed by glycerol shock as described in Materials and Methods. After four days of growth in DMEM +10% FBS, the transfected cells were replated either at $5 \times 10^3$ cells per 100 mm plate (master cultures), or at $1 \times 10^3$ cells per 100 mm plate (for individual clones), and selected for cells that had taken up DNA by the addition of hygromycin-B (200 ug/ml final concentration) to the growth medium. Conditioned media from cultures resistant to hygromycin-B were assayed two weeks later for human gamma-IFN using a biological assay which specifically measures a reduction in the cytopathic effect of EMC virus on human WISH cells.

Nine master cultures transfected by p222 DNA and resistant to hygromycinB were examined using the biological assay, and all were found to express and secrete gamma-IFN in a range of 4500 to 8500 U/ml in 24 hours (average=6600 U/ml). In order to assess the stability of gamma-IFN expression over time, four of the nine master cultures were assayed biweekly for a period of two months. Expression was found to be stable over this time period, but only if the cells were maintained in medium containing hygromycin-B. A decrease in expression was observed, even after a single passage in medium without hygromycin-B.

Deposit of Strains Useful in Practicing the Invention (A) Cultures of the following strain/plasmids are held by the inventors at Meloy Laboratories, Inc., 6715 Electronic Drive, Springfield, VA 22151.

(B) Access to said culture will be available during pendency of the patent application to one determined by the Commissioner to be entitled thereto under 37 C.F.R. Section 1.14 and 35 U.S.C. Section 122.

(C) A deposit of biologically pure cultures of the following strains will be made at the proper time with the American Type Culture Collection, 12301 Parklawn Drive, Rockville, Md. an accession number to be indicated will be assigned after successful viability testing, and the requisite fees are paid.

(D) All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Plasmid | ATTC No. | Deposit Date |
| --- | --- | --- |
| p222(pEBV-gamma-IFN) | 68185 | November 28, 1989 |
| p239(pEBV-gamma-IFN) | 68184 | November 28, 1989 |
| p147(pEBV-gamma-IFN) | 68186 | November 28, 1989 |

We claim:

1. An Epstein-Barr virus based expression vector having the identifying characteristics of p222 (pEBv-gamma-IFN), p239 (pEBV-gamma-IFN), or p147 (pEBV-gamma-IFN).

2. A host cell transformed by a vector of claim 1.

3. A recombinant DNA expression vector comprising:
   an Epstein-Barr virus origin of replication;
   an EBNA-1 gene; and
   a human gamma interferon expression cassette comprising a promoter region, an open reading frame encoding human gamma interferon and a polyadenylation region.

4. The vector of claim 3, wherein said human gamma interferon expression cassette and said EBNA-1 gene are oriented in the same transcriptional direction.

5. The vector of claim 4, comprising a selectable marker expression cassette, and wherein said human gamma interferon expression cassette includes an enhancer region.

6. The vector of claim 5, wherein said enhancer region is selected from the group consisting of M-MSV enhancer and H-CMV enhancer.

7. The vector of claim 6, wherein said promoter region is selected from the group consisting of M-MT promoter and SV40 early promoter.

8. The vector of claim 7, wherein said selectable marker expression cassette comprises a hygromycin phosphotransferase expression cassette 9. The vector of claim 8, comprising a multiple cloning site.

10. The vector of claim 9, wherein said multiple cloning site is derived from pUC12.

11. The vector of claim 10, comprising a prokaryotic replicon.

12. The vector of claim 11, wherein said prokaryotic replicon is derived from pBR322.

13. A mammalian host cell transformed by the vector of claim 3.

14. A mammalian host cell transformed by the vector of claim 12.

15. The host cell of claim 13, wherein said host cell is capable of expressing and secreting human gamma interferon at a rate between about 4500 and about 8500 U/ml/day.

16. The hoet cell of claim 14, wherein said host cell is capable of expressing and secreting human gamma interferon at a rate between about 4500 and about 8500 U/ml/day.

17. A process for producing human gamma interferon comprising:

providing a stable, extrachromosomally replicable vector capable of directing the expression of a DNA sequence encoding human gamma interferon in mammalian cells, said vector comprising a cis-acting Epstein-Barr virus origin of replication; a trans-acting EBNA-1 gene; a pUC12 multiple cloning site; a selectable marker expression cassette oriented in an opposite transcriptional direction as said EBNA-1 gene and comprising a hygromycin phosphotransferase expression cassette; a human gamma interferon expression cassette oriented in the same transcriptional direction as said EBNA-1 gene and comprising, in order of transcription, an enhancer region selected from the group consisting of M-MSV and H-CMV enhancer, a promoter region selected from the group consisting of M-MT promoter and SV40 early promoter, a nucleotide sequence encoding human gamma interferon and an SV40-derived polyadenylation sequence;

transforming said mammalian cells with said vector; and maintaining said transformed mammalian cells under conditions permitting the expression of said human gamma interferon.

18. The process of claim 17, wherein said vector is selected from the group consisting of p147, p222 and p239.

19. The process of claim 17, further comprising the step of recovering said human gamma interferon.

20. The process of claim 18, further comprising the step of recovering said human gamma interferon.

* * * * *